(12) United States Patent
Carey et al.

(10) Patent No.: US 6,448,280 B1
(45) Date of Patent: Sep. 10, 2002

(54) ANGIOTENSIN II ANTAGONISTS AGAINST DISORDERS ASSOCIATED WITH IMPAIRED NEURONAL CONDUCTION VELOCITY, ESPECIALLY DIABETIC NEUROPATHY

(75) Inventors: Frank Carey, Wilmslow; Alexander Anthony Oldham, Stockport; Norman Eugene Cameron; Mary Anne Cotter, both of Aberdeen, all of (GB)

(73) Assignee: Zeneca Limited, London (GB)

( * ) Notice: Subject to any disclaimer, the term of this patent is extended or adjusted under 35 U.S.C. 154(b) by 0 days.

(21) Appl. No.: 08/313,194

(22) PCT Filed: Apr. 7, 1993

(86) PCT No.: PCT/GB93/00732

§ 371 (c)(1),
(2), (4) Date: Jan. 5, 1995

(87) PCT Pub. No.: WO93/20816

PCT Pub. Date: Oct. 28, 1993

(30) Foreign Application Priority Data

Apr. 13, 1992 (GB) .............................................. 9208116

(51) Int. Cl.$^7$ ...................... A61K 31/41; A61K 31/55; A61K 31/44
(52) U.S. Cl. .................. 514/381; 514/382; 514/214.02; 514/213; 514/314; 514/337
(58) Field of Search ................................. 514/381, 382, 514/214.02, 213, 314, 337

(56) References Cited

U.S. PATENT DOCUMENTS

| | | | |
|---|---|---|---|
| 5,049,565 A | 9/1991 | Shieh-Shung et al. | 514/302 |
| 5,175,164 A | * 12/1992 | Bagley et al. | 514/259 |

FOREIGN PATENT DOCUMENTS

| | | |
|---|---|---|
| EP | 412848 | 2/1991 |
| EP | 434259 | 6/1991 |
| EP | 516392 | 12/1992 |
| EP | 528762 | 2/1993 |
| WO | 91 14367 | 10/1991 |
| WO | 92 10182 | 6/1992 |
| WO | 92 10183 | 6/1992 |

OTHER PUBLICATIONS

Cameron et al., Angiotensin converting enzyme inhibition prevents development of muscle and nerve dysfunction and stimulates angiogenesis in streptozocin–diabetic rats, Diabetologia, 1992, pp. 12–18.

Barnes et al., Angiotensin II Inhibits Cortical Cholinergic Function: Implications for Cognition, Journal of Cardiovascular Pharmacology, 1990, pp. 234–238.

Camargo et al, Control of blood pressure and end–organ damage in maturing salt–loaded stroke–prone spontaneously hypertensive rats by oral angiotensin II receptor blockade, Journal of Hypertension, 1993, pp. 31–40.

* cited by examiner

*Primary Examiner*—Theodore J. Criares
(74) *Attorney, Agent, or Firm*—Morgan, Lewis & Bockius LLP

(57) ABSTRACT

This invention relates to the use of angiotensin II antagonists in treating or preventing the development of disease conditions associated with impaired neuronal conduction velocity, such as diabetic neuropathy, as well as their use in the manufacture of a medicament for use in such treatment. The invention also concerns pharmaceutical compositions containing an angiotensin II antagonist together with one or more other agents known to be of value in treating or preventing the development of disease conditions associated with impaired neuronal conduction velocity.

6 Claims, No Drawings

ANGIOTENSIN II ANTAGONISTS AGAINST DISORDERS ASSOCIATED WITH IMPAIRED NEURONAL CONDUCTION VELOCITY, ESPECIALLY DIABETIC NEUROPATHY

TECHNICAL FIELD

This invention relates to therapeutic agents and in particular to the use of compounds having angiotensin II antagonist activity (hereinafter "AII antagonists") for the treatment or prevention of disease conditions associated with impaired neuronal conduction velocity in warm-blooded animals including man. The invention also concerns the use of a compound having AII antagonist activity in the production of a medicament for use in the treatment or prevention of disease conditions associated with impaired neuronal conduction velocity. The invention further concerns a method of treating or preventing disease conditions associated with impaired neuronal conduction velocity by administration of an AII antagonist to a warm blooded animal (including man).

BACKGROUND TO INVENTION

Impaired neuronal conduction velocity is a feature of nerve dysfunction commonly found, for example, in diabetic patients, and in disease conditions, such as alcoholic, toxic or compression neuropathy. Consequently an agent which prevents or reverses impairment of nerve conduction velocity may have a beneficial effect in the treatment or prevention of such medical conditions in which nerve conduction velocity is reduced, for example, diabetic neuropathy. We have now surprisingly discovered that impaired neuronal conduction velocity in a diabetic rat is significantly reversed by administration of an AII antagonist.

DISCLOSURE OF INVENTION

According to the invention there is provided a method of treating or preventing the development of disease conditions associated with impaired neuronal conduction velocity in a warm-blooded animal (including a human being) requiring such treatment which comprises administering to said animal a therapeutically effective amount of an AII antagonist, or a pharmaceutically acceptable salt thereof.

Typical AII antagonists useful in the invention include:

(a) 2-butyl-4-chloro-5-hydroxymethyl-1-[(2'-(1H-tetrazol-5-yl)biphenyl-4-yl)methyl]imidazole described in European Patent Application (EPA), Publication No. 253310;
(b) 2-butyl-3-(2'-(1H-1,2,3,4-tetrazol-5-yl)biphenyl-4-yl)-methyl-3H-imidazo[4,5-b]pyridine described in EPA, Publication No. 399731;
(c) 5,7-dimethyl-2-ethyl-3-(2'-(tetrazol-5-yl)biphenyl-4-yl)-methyl-3H-imidazo[4,5-b]pyridine described in EPA, Publication No. 400974;
(d) 1-[[3-bromo-2-[2-(1H-tetrazol-5-yl)phenyl]-5-benzofuranyl]-methyl-2-butyl-4-chloro-1H-imidazole-5-carboxylic acid described in EPA, Publication No. 434249;
(e) 2-ethyl-4-[(2'-(1H-1,2,3,4-tetrazol-5-yl)biphenyl-4-yl)-methoxy]quinoline described in EPA, Publication No. 412848; and
(f) 2-ethyl-5,6,7,8-tetrahydro-4-[(2'-(1H-1,2,3,4-tetrazol-5-yl)biphenyl-4-yl)methoxy]quinoline described in EPA, Publication No. 453210;
(g) 5,7-diethyl-1-[(2'-(1H-tetrazol-5-yl)biphenyl-4-yl) methyl]-1,6-naphthyridin-2(1H)-one described in EPA, Publication No. 516392; and
(h) 5,7-diethyl-1-[(2'-(1H-tetrazol-5-yl)biphenyl-4-yl) methyl]-1,2,3,4-tetrahydro-1,6-naphthyridin-2-one described in EPA, Publication No. 516392;

and the pharmaceutically acceptable salts thereof.

Further AII antagonists include those described in EPA, Publication Nos. 253310, 323841, 324377, 399731, 400974, 401030, 403158, 403159, 407102, 407342, 409332, 411507, 411766, 412594, 412848, 415886, 419048, 420237, 424317, 425921, 425211, 426021, 427463, 429257, 430709, 430300, 434249, 432737, 434038, 435827, 437103, 438869, 442473, 443983, 443568, 445811, 446062, 449699, 450566, 453210, 454511, 454831, 456442, 459136, 456442, 456510, 461039, 461040, 465323, 465368, 467207, 467715, 468372, 468470, 470543, 475206, 475898, 479479, 480204, 480659, 481448, 481614, 483683, 485929, 487252, 487745, 488532, 490587, 490820, 492105, 497121, 497150, 497516, 498721, 498722, 498723, 499414, 499415, 499416, 500297, 500409, 501269, 501892, 502314, 502575, 502725, 503162, 503785, 503838, 504888, 505098, 505111, 505893, 505954, 507594, 508393, 508445, 508723, 510812, 510813, 511767, 511791, 512675, 512676, 512870, 513533, 513979, 514192, 514193, 514197, 514198, 514216; 514217, 515265, 515357, 515535, 515546, 515548, 516392, 517357, 517812, 518033, 518931, 520423, 520723, 520724, 521768, 522038, 523141, 526001, 527534, and 528762. Other AII antagonists include those disclosed in International Patent Application, Publication Nos. WO 91/00277, WO 91/00281, WO 91/11909, WO 91/11999, WO 91/12001, WO 91/12002, WO 91/13063, 91/15209, WO 91/15479, WO 91/16313, WO 91/17148, WO 91/18888, WO 91/19697, WO 91/19715, WO 92/00067, WO 92/00068, WO 92/00977, WO 92/02510, WO 92/04335, WO 92/04343, WO 92/05161, WO 92/06081, WO 92/07834, WO 92/07852, WO 92/09278, WO 92/09600, WO 92/10189, WO 92/11255, WO 92/14714, WO 92/16523, WO 92/16552, WO 92/17469, WO 92/18092, WO 92/19211, WO 92/20651, WO 92/20660, WO 92/20687, WO 92/21666, WO 92/22533, WO 93/00341, WO 93/01177, WO 93/03018, WO 93/03033 and WO 93/03040. The contents of the aforesaid European and International Patent Applications are hereby incorporated by reference thereto.

Prior to the present invention, AII antagonists have been described as having use in, for example, the treatment of hypertension and congestive heart failure. However there has been no suggestion that a compound possessing AII antagonist activity might be useful in treating or preventing impaired nerve conduction velocity.

According to a further aspect of the invention there is provided the use of an AII antagonist, or a pharmaceutically acceptable salt thereof, for the manufacture of a medicament for use in the treatment or prevention of the development of disease conditions associated with impaired neuronal conduction velocity.

According to a further aspect of the invention there is provided a method of reversing impaired neuronal conduction velocity in a warm-blooded animal (including a human being) requiring such treatment which comprises administering to said animal a therapeutically effective amount of a compound having AII antagonist activity, or a pharmaceutically acceptable salt thereof.

According to a further aspect of the invention there is provided the use of a compound having AII antagonist activity, or a pharmaceutically acceptable salt thereof, for the manufacture of a medicament for use in the reversal of impaired neuronal conduction velocity.

According to a further aspect of the invention there is provided a method of treating or preventing diabetic neuropathy in a warm-blooded animal (including a human being) requiring such treatment which comprises administering to said animal a therapeutically effective amount of a compound having AII antagonist activity, or a pharmaceutically acceptable salt thereof.

According to a further aspect of the invention there is provided the use of a compound having AII antagonist activity, or a pharmaceutically acceptable salt thereof, for the manufacture of a medicament for use in the treatment or prevention of diabetic neuropathy.

Preferred AII antagonists for use in the invention include:

(i) 2-butyl-4-chloro-5-hydroxymethyl-1-[(2'-(1H-tetrazol-5-yl)-biphenyl-4-yl)methyl]imidazole;
(ii) 2-ethyl-4-[(2'-(1H-1,2,3,4-tetrazol-5-yl)biphenyl-4-yl)methoxy]-quinoline;
(iii) 2-ethyl-5,6,7,8-tetrahydro-4-[(2'-(1H-1,2,3,4-tetrazol-5-yl)-biphenyl-4-yl)methoxy]quinoline;
(iv) 5,7-diethyl-1-[(2'-(1H-tetrazol-5-yl)biphenyl-4-yl)methyl]-1,6-naphthyridin-2(1H)-one; and
(v) 5,7-diethyl-1-[(2'-(1H-tetrazol-5-yl)biphenyl-4-yl)methyl]-1,2,3,4-tetrahydro-1,6-naphthyridin-2-one;

and the pharmaceutically acceptable salts thereof.

A particularly preferred AII antagonist is compound (ii).

A preferred pharmaceutically acceptable salt of compound (i) is, for example, an alkali metal salt, especially the potassium salt.

A preferred pharmaceutically acceptable salt of compound (ii), (iii), (iv) or (v) is, for example, an acid addition salt, especially the hydrochloride salt.

The AII antagonists and their pharmaceutically acceptable salts may be obtained, for example, by the methods given in the relevant published European and International patent applications referred to above.

In use, an AII antagonist (or a pharmaceutically acceptable salt thereof) will generally be administered for its treatment or prevention of the development of impaired neuronal conduction velocity in a warm-blooded animal (including a human being) requiring such treatment in the form of a conventional pharmaceutical composition, for example, as may be described in the relevant published European or International patent applications referred to above, and generally in a form suitable for oral administration (e.g. as a tablet, capsule, suspension or solution). It will be appreciated that an AII antagonist may be administered together with one or more pharmaceutical agents known in the general art to be of value in treating or preventing medical conditions in which neuronal conduction velocity is reduced, such as diabetic neuropathy. In the latter case a particularly suitable pharmaceutical agent may be, for example, an aldose reductase inhibitor or hypoglycaemic agent. The invention thus also includes pharmaceutical compositions (to include, for example, a combination preparation for simultaneous, separate or sequential use) containing an AII antagonist together with one or more pharmaceutical agents known in the general art to be of value in treating or preventing the development of disease conditions associated with impaired neuronal conduction velocity.

In general, the AII antagonist (or a pharmaceutically acceptable salt thereof) will be administered to man so that, for example a daily oral dose of up to 50 mg/kg body weight (and preferably of up to 10 mg/kg) or a daily parenteral dose of up to 5 mg/kg body weight (and preferably of up to 1 mg/kg) is received, given in divided doses as necessary. However, it will be readily understood that it may be necessary to vary the dose of therapeutic agent administered in accordance with well known medical practice to take account of the nature and severity of the impaired neuronal conduction velocity under treatment and the age, weight and sex of the patient receiving the treatment.

The effects of a representative compound for use in a method according to the invention are described in the following non-limiting example:

EXAMPLE 1

Using an analogous method to that described by Cameron et al in Quarterlty Journal of Experimental Physiology, 1989, 74, 917–926, mature male rats were divided into non-diabetic animals (normal control group) and animals rendered diabetic (by administration of streptozotocin (40–45 mg/kg in 20 mmol/l sodium citrate buffer, pH 4.5, i.p.). The diabetic animals were further divided into two groups. After one month, the motor nerve conduction velocities in one of the diabetic groups (diabetic control group 1) were measured in vivo between the sciatic notch and the knee for motor branches supplying the gastrocnemius and tibialis anterior muscles of the calf using the procedures described by Cameron et al (ibid) (further details of the procedures are given in Experimental Neurology, 1986, 92, 757–761). Sensory nerve conduction velocity was also measured for diabetic control group 1 in the saphenous nerve between the groin and ankle (again using the method of Cameron et al (ibid)). The remaining group of diabetic animals was further divided into two groups. One of these groups was given daily 2-ethyl-4-[(2'-(1H-1,2,3,4-tetrazol-5-yl)biphenyl-4-yl)methoxy]quinoline hydrochloride (Compound A; 50 mg/kg) by gavage, the other group remaining untreated (diabetic control group 2). After a further month, motor and sensory nerve conduction velocities were obtained as before for both the treated group and diabetic control group 2. These values were compared with the corresponding nerve conduction velocities which had been obtained for the normal control group at the beginning of the study. The following nerve conduction velocities (NCV) were obtained in the relevant sciatic branches and in the saphenous nerve:

| Group | n | Motor NCV Gastrocnemius (m/s) | Motor NCV Tibialis Anterior (m/s) | Sensory NCV Saphenous (m/s) |
| --- | --- | --- | --- | --- |
| Normal control | 20 | 65.4 ± 1.9 | 65.1 ± 1.9 | 59.3 ± 1.3 |
| Diabetic control Group 1 (1 month) | 12 | 52.4 ± 1.8 | 51.0 ± 1.4 | 50.7 ± 1.0 |
| Group 2 (2 months) | 20 | 50.7 ± 1.3 | 41.7 ± 2.2 | 52.1 ± 1.2 |
| Diabetic + Compound A | 12 | 62.8 ± 0.9 | 60.3 ± 1.2 | 60.2 ± 1.1 |

(n = number of animals in group)

What is claimed is:

1. A method of treating a disease condition associated with impaired neuronal conduction velocity in a warm-blooded animal requiring such treatment which comprises administering to said animal a neuronal conduction velocity enhancing effective amount of an angiotensin II antagonist, or a pharmaceutically acceptable salt thereof.

2. A method of reversing impaired neuronal conduction velocity in a warm-blooded animal requiring such treatment which comprises administering to said animal a neuronal conduction velocity enhancing effective amount of a compound having angiotensin II antagonist activity, or a pharmaceutically acceptable salt thereof.

3. A method of treating diabetic neuropathy in a warm-blooded animal requiring such treatment which comprises administering to said animal a neuronal conduction velocity enhancing effective amount of a compound having angiotensin II antagonist activity, or a pharmaceutically acceptable salt thereof.

4. A method as claimed in claim 1, 2 or 3 wherein the AII antagonist is selected from:

(a) 2-butyl-4-chloro-5-hydroxymethyl-1-[(2'-(1H-tetrazol-5-yl)biphenyl-4-yl)methyl]imidazole;
(b) 2-butyl-3-(2'-(1H-1,2,3,4-tetrazol-5-yl)biphenyl-4-yl)-methyl-3H-imidazo[4,5-b]pyridine;
(c) 5,7-dimethyl-2-ethyl-3-(2'-(tetrazol-5-yl)biphenyl-4-yl)-methyl-3H-imidazo[4,5-b]pyridine;
(d) 1-[[3-bromo-2-[2-(1H-tetrazol-5-yl)phenyl]-5-benzofuranyl]-methyl-2-butyl-4-chloro-1H-imidazole-5-carboxylic acid;
(e) 2-ethyl-4-[(2'-(1H-1,2,3,4-tetrazol-5-yl)biphenyl-4-yl)-methoxy]quinoline;
(f) 2-ethyl-5,6,7,8-tetrahydro-4-[(2'-(1H-1,2,3,4-tetrazol-5-yl)biphenyl-4-yl)methoxy]quinoline;
(g) 5,7-diethyl-1-[(2'-(1H-tetrazol-5-yl)biphenyl-4-yl)methyl]-1,6-naphthyridin-2(1H)-one; and
(h) 5,7-diethyl-1-[(2'-(1H-tetrazol-5-yl)biphenyl-4-yl)methyl]-1,2,3,4-tetrahydro-1,6-naphthyridin-2-one;

or a pharmaceutically acceptable salt thereof.

5. A method as claimed in claim 1, 2 or 3 wherein the AII antagonist is 2-ethyl-4-[(2'-(1H-1,2,3,4-tetrazol-5-yl)biphenyl-4-yl)-methoxy]quinoline, or a pharmaceutically acceptable salt thereof.

6. A pharmaceutical composition comprising an angiotensin II antagonist, or a pharmaceutically acceptable salt thereof, together with one or more pharmaceutical agents selected from aldose reductase inhibitors and hypoglycaemic agents.

\* \* \* \* \*